US00RE43914E

(19) United States
(12) Reissued Patent
Castro

(10) Patent Number: US RE43,914 E
(45) Date of Reissued Patent: Jan. 8, 2013

(54) METHOD FOR DETECTING SYPHILIS USING SYNTHETIC ANTIGENS

(75) Inventor: Arnold R. Castro, Monroe, GA (US)

(73) Assignee: The United States of America as represented by the Secretary of the Department of Health and Human Services, Centers for Disease Control and Prevention, Washington, DC (US)

(21) Appl. No.: 13/333,849

(22) Filed: Dec. 21, 2011

Related U.S. Patent Documents

Reissue of:
(64) Patent No.: 6,815,173
Issued: Nov. 9, 2004
Appl. No.: 10/009,698
PCT Filed: Jun. 8, 2000
PCT No.: PCT/US00/15828
§ 371 (c)(1),
(2), (4) Date: Dec. 5, 2001
PCT Pub. No.: WO00/75666
PCT Pub. Date: Dec. 14, 2000

U.S. Applications:
(60) Provisional application No. 60/138,192, filed on Jun. 9, 1999.

(51) Int. Cl.
*G01N 33/571* (2006.01)
*G01N 33/543* (2006.01)
*C12N 15/09* (2006.01)
*A61K 39/02* (2006.01)

(52) U.S. Cl. .... 435/7.36; 435/69.3; 436/518; 424/262.1

(58) Field of Classification Search ..... None
See application file for complete search history.

(56) References Cited

U.S. PATENT DOCUMENTS

| | | | | |
|---|---|---|---|---|
| 4,307,074 | A | | 12/1981 | Barner et al. |
| 4,738,932 | A | | 4/1988 | Yabusaki |
| 5,919,633 | A | | 7/1999 | Tausk et al. |
| 5,994,149 | A | | 11/1999 | Robinson et al. |
| 6,146,659 | A | * | 11/2000 | Rahman ..... 424/450 |

FOREIGN PATENT DOCUMENTS

| | | | | |
|---|---|---|---|---|
| GB | 1053504 | | | 3/1964 |
| JP | 74046051 | B | * | 7/1974 |
| JP | 74046051 | B | | 12/1974 |
| JP | 05312808 | A | | 11/1993 |
| JP | 10239315 | | | 9/1998 |
| SE | 629927 | | * | 10/1978 |
| SU | 629927 | A | | 10/1978 |
| WO | WO 2004/040311 | A1 | | 5/2004 |

OTHER PUBLICATIONS

Avanti Polar Lipids; retreived from web 2012; structure of egg phosphatidylcholine.*
Allen and Mason, "Cardiolipin Antigens in the Serodiagnosis of Syphilis," *Canadian J. Public Health* 43:128-135, 1952.
Avanti Polar Lipids Inc. Products # 850457 and 710332, printed from internet Feb. 24, 2005.
Browne et al., "An Evaluation of the Cardiolipin-Synthetic Lecithin Kline Test," *Technical Bulletin of the Registry of Medical Technologists* 33:171-176, 1963.
Castro et al., "Use of Synthetic Cardiolipin and Lecithin in the Antigen Used by the Venereal Disease Research Laboratory Test for Serodiagnosis of Syphilis," *Clin. Diag. Lab. Immunol.* 7:658-661, 2000.
de Haas and van Deene, "Chemical Structure and Serological Activity of Synthetic and Natural Cardiolipin," *Nature* 206:935, 1965.
Faure and Coulon-Marelec, "Role de la Lécithine dans l'immunoagglutination des Particules de Cholesterol Sensibilisées avec un Haptène Lipidique," *Biochimie* 56:263-268, 1974. (in French, with English abstract.).
Gokhale et al., "An Improved Method of Encapsulation of Doxorubicin in Liposomes: Pharmacological, Toxicological and Therapeutic Evaluation," *Br. J. Cancer* 74:43-48, 1996.
Inoue and Nojima, "Immunochemical Studies of Phospholipids. III. Production of Antibody to Cardiolipin," *Biochim. Biophys. Acta* 144:409-414, 1967.
Inoue et al., "Immunochemical Studies of Phospholipids—IV: The Reactivities of Antisera Against Natural Cardiolipin and Synthetic Cardiolipin Analogues-Containing Antigens," *Chem. Phys. Lipids* 3:70-77, 1969.
Kennedy, Jr., E.J. And Creighton ET. Venereal Disease Research Laboratory (VDRL) Slide Tests. Chapter 8, pp. 159-178. In: Larsen SA, Pope, V., Johnson, R.E., and Kennedy, Jr., E.J., Eds. A Manual of Tests for Syphilis, 9th Ed. Amer. Public Health Assoc. Washington, DC, 1998.
Paris-Hamelin et al., "Immunoblotting for the Serodiagnosis of Syphilis. A Candidate to Replace the Nelson-Mayer Test," *Ann Pharm Fr.* 57:68-75, Abstract, 1999.
Tonks and Allen, "The Use of Some Synthetic Phospharides in Antigens for the Serodiagnosis of Syphilis," *Science* 118:55-56, 1953.
Wicher et al., "Autoimmunity in Syphilis," *Immunol Ser.* 52:101-124, Abstract, 1990.
Borovyagin et al., "Model Membrane Morphology and Crosslinking of Oxidized Lipids with Proteins," *J. Ultrastruct. Res.* 89:261-273, 1984.
Avanti Polar Lipids Inc. Products # 850457 and 710332.*
Gokhale et al. British Journal of Cancer, vol. 74, pp. 43-48 1996.*
Gokhale, P.C. et al., "An Improved Method of Encapsulation of Doxorubicin in Liposomes: Pharmacological, Toxicological and Therapeutic Evaluation," *British Journal of Cancer,* vol. 74, No. 1, pp. 43-48 (1996).
Inoue, K. et al., "Immunochemical Studies of Phospholipids—IV: The Reactivities of Antisera Against Natural Cardiolipin and Synthetic Cardiolipin Analogues-Containing Antigens," *Chemistry and Physics of Lipids,* vol. 3, No. 1, pp. 70-77 (1969).

(Continued)

*Primary Examiner* — Patricia A Duffy
(74) *Attorney, Agent, or Firm* — Klarquist Sparkman, LLP

(57) ABSTRACT

An antigen composition and method for the detection of antibodies to Treponema pallidum and the diagnosis of syphilis are described. The antigen composition contains synthetic cardiolipin and synthetic lecithin. The antigen composition may additionally contain cholesterol and an alcohol. The antigen composition is useful as an immunoreagent in immunoassays for the detection of antibodies associated with T. pallidum infection. The methods are sensitive and specific for T. pallidum infection.

24 Claims, No Drawings

OTHER PUBLICATIONS

Browne, A.S. et al., "An Evaluation of the Cardiolipin-Synthetic Lecithin Kline Test," *Technical Bulletin of the Registry of Medical Technologists,* vol. 33, No. 10, pp. 171-176 (Oct. 1963).

Castro, A.R. et al., "Use of Synthetic Cardiolipin and Lecithin in the Antigen Used by the Venereal Disease Research Laboratory Test for Serodiagnosis of Syphilis," *Clinical and Diagnostic Laboratory Immunology,* vol. 7, No. 4, pp. 658-661 (Jul. 2000).

Wicher, K. et al., "Autoimmunity in Syphilis," *Immunol Ser,* vol. 52, pp. 101-124, Abstract (1990).

Paris-Hamelin, A. et al., "[Immunoblotting for the Serodiagnosis of Syphilis. A Candidate to Replace the Nelson-Mayer Test,]" Ann Pharm Fr., vol. 57, No. 1, pp. 68-75, Abstract (1999).

Larsen, S.A. et al., *A Manual of Tests for Syphilis, 9th* Ed., American Public Health Association, Washington, D.C., pp. 157-178.

* cited by examiner

METHOD FOR DETECTING SYPHILIS USING SYNTHETIC ANTIGENS

Matter enclosed in heavy brackets [ ] appears in the original patent but forms no part of this reissue specification; matter printed in italics indicates the additions made by reissue.

PRIORITY CLAIM

This is a §371 U.S. National Stage of PCT/US00/15828, filed Jun. 8, 2000, which was published in English under PCT Article 21(2), which claims the benefit of U.S. Provisional Application 60/138,192, filed Jun. 9, 1999.

FIELD OF THE INVENTION

The present invention relates to the fields of microbiology and immunology and more specifically relates to compositions and methods for detecting, diagnosing and monitoring the treatment of syphilis. In particular, the invention pertains to synthetic cardiolipin and lecithin antigen compositions and their use in immunoassays.

BACKGROUND OF THE INVENTION

Syphilis is a sexually transmitted disease (STD) caused by the bacterium Treponema pallidum. Over 100,000 cases of adult syphilis are reported worldwide each year. The disease is also transmitted congenitally, affecting 3000 or more infants annually. Failure to obtain antibiotic treatment in the early stages of the disease allows progression of the disease throughout the body, often resulting in irreversible damage to organs, insanity, blindness, or death. The spread of the human immunodeficiency virus (HIV) around the world has greatly amplified the severity of syphilis as a health problem because genital ulcers produced during the early stages of syphilis infection facilitate the sexual transmission of HIV.

The course of syphilis has been divided into stages; primary, secondary, latent, neurosyphilis and tertiary (late). An infected individual may infect others during the first two stages. Transmission occurs when bacteria are spread from the ulcer of an infected person to the skin or mucous membranes of the genital area, mouth, or anus of a sexual partner. T. pallidum organisms can also pass through broken skin on other parts of the body. In tertiary syphilis and neurosyphilis, the bacterial infection is not contagious, but the invasion of the organism into the organs, tissues, and brain can have fatal consequences such as serious cardiovascular abnormalities or neurologic disease.

Vertical or transplacental syphilis infection can occur during the first four years a pregnant woman is infected and not treated. Although adequate treatment of the mother usually prevents congenital syphilis, approximately 25% of human fetuses that have been exposed to T. pallidum infection in utero are reported as stillbirth deaths. Some infants with congenital syphilis have symptoms at birth, but most develop symptoms two to three months post partum. These symptoms include skin sores, rashes, fever, swollen liver and spleen, jaundice, anemia, and various deformities. As infected infants mature, they may develop the symptoms of late-stage syphilis including irreversible damage to bones, teeth, eyes, ears, and brain.

The first symptom of primary syphilis is an ulcer, or chancre. The chancre appears within ten days to three months after exposure and is usually found on the part of the body that was exposed to the ulcer of an infected sexual partner, such as the penis, vulva, vagina, cervix, rectum, tongue, or lip. Because the chancre lasts only a few weeks and may be painless or occur inside the body, it may go unnoticed. The chancre disappears with or without treatment. In persons who are untreated, secondary symptoms will appear approximately nine weeks after the appearance of the primary lesion.

Secondary syphilis is often marked by a skin rash that is characterized by brown sores approximately the size of a penny. Because active bacteria are present in these sores, any physical contact, sexual or non-sexual, with the broken skin of an infected individual may spread the infection at this stage. Other symptoms include mild fever, fatigue, headache, sore throat, patchy hair loss, and swollen lymph glands. These symptoms may be mild and, like the chancre of primary syphilis, will disappear with or without treatment. If untreated, the infected person then enters a period of latency.

Latent syphilis is characterized by the absence of clinical signs or abnormal findings in cerebrospinal fluid (CSF) in conjunction with positive results of serologic tests. Early latent syphilis, which occurs within one year of infection, is potentially transmissible and relapses may occur, while late latent syphilis is associated with immunity to relapse and resistance to re-infection.

During the early stages of syphilis infection, the bacteria may invade the nervous system. If left untreated, neurosyphilis may develop. Progression of the disease to neurosyphilis may take up to twenty years, and some individuals having neurosyphilis fail to develop recognizable symptoms, making diagnosis very difficult. Those who do present symptoms may complain of headache, stiff neck, or fever, which result from an inflammation of the lining of the brain. Seizures and symptoms of stroke such as numbness, weakness, or visual problems may also afflict neurosyphilis patients.

Although approximately two-thirds of T. pallidum-infected individuals who fail to obtain treatment will suffer no further consequences of the disease, approximately one-third of those with untreated latent syphilis develop the complications of late, or tertiary, syphilis. In the tertiary stage of syphilis, the bacteria damage the heart, eyes, brain, nervous system, bones, joints, or almost any other part of the body. The tertiary stage can last for years, or even decades. Late syphilis commonly results in cardiovascular disease, mental illness, blindness, or even death.

Due to the sometimes serious and life threatening effects of syphilis infection, and the risk of transmitting or contracting HIV, specific and early diagnosis of the infection is essential. Syphilis, however, has sometimes been referred to as "the great imitator" because its early symptoms are similar to those of many other diseases. Therefore, a physician usually does not depend solely on a recognition of the signs and symptoms of syphilis, but relies on the results of clinical tests including the microscopic identification of syphilis bacteria and analytical tests for manifestations of syphilis infection in biological samples.

Diagnosis of syphilis by microscopic identification of the bacteria is performed generally as follows. A scraping is taken from the surface of the ulcer or chancre and is examined under a special "dark-field" microscope to detect the organism. Dark-field microscopy requires considerable skill and is prone to misinterpretation.

For these reasons, most cases of syphilis are first diagnosed serologically using non-treponemal assays. Non-treponemal tests detect substances, such as antibodies, that are produced in the presence of a T. pallidum infection. The currently available non-treponemal assays most often used to detect evidence of a syphilis infection are the Venereal Disease Research Laboratory (VDRL) test and the rapid plasma reagin (RPR) test. The VDRL test employs lipids obtained from naturally-occurring sources, to detect anti-lipoidal antibodies that are generated upon infection by T. pallidum. These antibodies are generated against the cardiolipin of the T. pallidum organism by the immune system of the individual infected with T. pallidum and may be found in the serum or cerebrospinal fluid of the individual.

One disadvantage to the presently available non-treponemal tests is poor specificity. Many medical conditions, including mycoplasma infection, pneumonia, malaria, acute bacterial and viral infections, and autoimmune disease can cause false positive test results in presently available tests for syphilis. For example, intravenous drug use or autoimmune disease causes tissue damage, which results in the release of cardiolipin and the production of anti-cardiolipin antibodies. Detection of these anti-cardiolipin antibodies in a non-treponemal test would therefore produce a false positive result. Successful diagnosis is particularly problematic for the detection of neurosyphilis.

Due to the occurrence of false positive and false negative results when using these existing tests, confirmation using an alternative method of analysis, such as microscopy or a treponemal-based serological test, is normally required. Standard treponemal-based tests include the fluorescent treponemal antibody-absorption (FTA-ABS) test and the FTA-ABS double staining test (FTA-ABS DS). Although treponemal-based assays may be used to confirm a positive test result, these tests are often expensive, complicated, and time consuming, and may require the use of highly sophisticated scientific instrumentation and trained scientific personnel. In addition, treponemal assays cannot be used as tests to monitor the success of antibiotic therapy because, due to the continued presence of anti-T. pallidum antibodies after cure, the tests results remain positive even after eradication of the infection for approximately 85% of successfully treated individuals.

Therefore, a single assay for the sensitive and specific detection of T. pallidum infection in a sample for the diagnosis of early stage syphilis or neurosyphilis is needed. Also needed is a simple, inexpensive assay that can be used to monitor the success of syphilis treatment.

SUMMARY OF THE INVENTION

An antigen composition and method for detecting Treponema pallidum infection and thereby diagnosing syphilis are provided. The antigen composition contains a combination or mixture of synthetic cardiolipin and synthetic lecithin. The preferred antigen composition also contains a cholesterol. The preferred antigen composition further includes an alcohol. The alcohol solubilizes the lipids in the antigen composition to form a suspension. The antigen composition is useful as a reagent in assays for the detection of antibodies associated with T. pallidum infection in a biological sample, particularly a body fluid such as serum or cerebrospinal fluid. Preferably, the antigen composition is an immunoassay reagent for the detection or measurement of antibodies associated with T. pallidum infection.

The more preferred antigen composition contains purified, synthetic cardiolipin, synthetic lecithin, natural or non-synthetic cholesterol, and an alcohol. The optimal purity of the synthetic cardiolipin and lecithin in the composition is 99% or greater. The optimal purity of the cholesterol is 98% or greater, or is ash free. Most preferably, the antigen composition contains tetramyristoyl cardiolipin, 1-palmitoyl-2-oleoyl-sn-glycero-3-phosphocholine, cholesterol, and absolute (100%) ethanol. The preferred concentration by volume of synthetic cardiolipin in the composition is between about 0.01-0.05%, or between approximately 0.02-0.04%, or more preferably 0.03%. The preferred concentration by volume of synthetic lecithin in the composition is between approximately 0.11-0.16%, more preferably 0.14%. The preferred concentration by volume of cholesterol in the composition is approximately 0.9%, and the remainder of the composition is the alcohol.

The antigen composition provided herein is also useful in general as an in vitro research tool for studying syphilis. More particularly, the composition is useful in assays or diagnostic kits to detect the presence of T. pallidum infection, which is diagnostic or prognostic for the occurrence or recurrence of syphilis disease.

The preferred method provided herein is an immunoassay for the detection of cardiolipin antibodies in a biological sample such as serum or cerebrospinal fluid. In accordance with the method, the antigen composition described herein is combined with the biological sample for a sufficient amount of time under conditions that facilitate the binding of anti-lipoidal antibodies in the sample to a synthetic cardiolipin-lecithin matrix, to form an antibody-antigen complex. This complex is then detected using methods well known to those skilled in the art such as flocculation or microflocculation tests, or the like.

Accordingly, it is an object of the present invention to provide a method for detecting carriers of T. pallidum infection and thus prevent the spread of T. pallidum from one host to another.

It is another object of the present invention to provide a sensitive method for the diagnosis of early or latent syphilis or neurosyphilis.

It is yet another object of the present invention to provide a rapid, simple, and inexpensive assay for the accurate detection of T. pallidum.

It is a further object of the present invention to provide an inexpensively produced antigen composition for the reproducible measurement or detection of T. pallidum.

It is another object of the present invention to provide a test for the detection of T. pallidum offers advantages in the standardization and stability of the VDRL antigen.

These and other objects, features, and advantages of the present invention will become apparent after a review of the following detailed description of the disclosed embodiments and the appended claims.

DETAILED DESCRIPTION

An antigen composition and method for the detection of Treponema pallidum are described herein. The antigen composition contains a mixture or combination of synthetic cardiolipin and synthetic lecithin. Cardiolipin is a 1,3-bis (phophatidyl)glycerol having antigenic properties. Lecithin is a phospholipid. The antigen composition preferably also includes a non-synthetic (natural) cholesterol. An alcohol is also a component of the preferred antigen composition. The alcohol solubilizes the lipids, thereby forming a suspension. The synthetic cardiolipin and lecithin have an optimal purity of 99% or greater. The cholesterol has an optimal purity of 98% or greater, or is ash free. The antigen composition is useful as a reagent in assays for the detection of antibodies associated with T. pallidum infection in a biological sample. Preferably, the antigen composition is an immunoassay reagent for the detection or measurement of antibodies generated in a patient infected with T. pallidum, which is diagnostic or prognostic for the occurrence or recurrence of syphilis.

The method described herein is an assay for the detection or quantitation of antibodies associated with infection of a patient by T. pallidum in a biological sample, particularly a body fluid sample such as serum or cerebrospinal fluid. The method permits detection of circulating antibodies associated with T. pallidum infection in order to detect or monitor a T. pallidum infection. A preferred method provided herein is an immunoassay. In accordance with the preferred method, the antigen composition is combined with the biological sample for a sufficient amount of time under conditions that facilitate the binding of anti-lipoidal antibodies in the sample to the cardiolipin in the antigen composition, to form antibody-antigen complexes. These antibody-antigen complexes are then detected using methods well known to those skilled in the art such as the VDRL flocculation or microflocculation test, which is read microscopically.

Definitions

The terms "a", "an" and "the" as used herein are defined to mean "one or more" and include the plural unless the context is inappropriate.

The term "antibodies" as used herein includes monoclonal antibodies, polyclonal, chimeric, single chain, bispecific, simianized, and humanized antibodies as well as Fab fragments, including the products of an Fab immunoglobulin expression library.

The phrases "specifically binds to" or "specifically immunoreactive with", when referring to an antibody, refers to a binding reaction which is determinative of the presence of the antigen of interest in the presence of a heterogeneous population of peptides, proteins, lipids and other biologics. Thus, under designated immunoassay conditions, the specified antigen or antigens bind preferentially to particular antibodies and do not bind in a significant amount to other antibodies present in the sample. Specific binding under such conditions requires an antigen that is selected for its specificity for a particular antibody. A variety of immunoassay formats may be used to select antigens specifically immunoreactive with a particular antibody. For example, solid-phase ELISA immunoassays are routinely used to select an antigen specifically immunoreactive with an antibody. See, Harlow and Lane (1988) Antibodies, A Laboratory Manual, Cold Spring Harbor Publications, New York, for a description of immunoassay formats and conditions that can be used to determine specific immunoreactivity.

The term "antigen" refers to an entity or fragment thereof which can induce an immune response in a mammal. The term includes immunogens and regions responsible for antigenicity or antigenic determinants. The term "antigen composition" as used herein refers to a composition containing synthetic cardiolipin and synthetic lecithin. "Antigenic determinant," as used herein, refers to a region of an antigen that is recognized by an antibody.

As used herein, the terms "detecting" or "detection" refers to qualitatively or quantitatively determining the presence of the biomolecule under investigation.

By "isolated" is meant a biological molecule free from at least some of the components with which it naturally occurs.

Antigen Compositions

The composition provided herein contains a combination, suspension or physical mixture of one or more synthetic cardiolipins and lecithins. A preferred composition contains synthetic cardiolipin, synthetic lecithin, and synthetic or non-synthetic (naturally occurring) cholesterol. The more preferred composition contains synthetic cardiolipin, synthetic lecithin, natural cholesterol, and an alcohol.

The preferred concentration of synthetic cardiolipin in the composition is between about 0.01-0.05% by volume, or between approximately 0.02-0.04% by volume, or more preferably 0.03% by volume. The preferred concentration of synthetic lecithin in the composition is between approximately 0.11 and 0.16% by volume, more preferably 14% by volume. The preferred concentration of natural cholesterol in the composition is approximately 0.9% by volume, and the remainder of the composition is alcohol, preferably ethanol, most preferably absolute (100%) ethanol.

The synthetic cardiolipin may be synthesized from semi-synthetic lipid precursors originating from plant sources. In a most preferred embodiment, the cardiolipin is tetramyristoyl cardiolipin, which is commercially available from sources such as Avanti Polar Lipids (Alabaster, Ala.).

The synthetic lecithin may be derived from soybeans or egg. In a preferred embodiment, the lecithin is a 16:0, 18:1 lecithin also described as 1-palmitoyl-2-oleoyl-sn-glycero-3-phosphocholine or 3-sn-phosphatidylcholine (sn means stereospecifically numbered), which is also available commercially from sources such as Avanti Polar Lipids (Alabaster, Ala.).

In a most preferred embodiment, the composition is a suspension containing approximately 0.03% tetramyristoyl cardiolipin, 0.11-0.16% 1-palmitoyl-2-oleoyl-sn-glycero-3-phosphocholine, and 0.9% natural cholesterol in absolute ethanol. The cholesterol is also available from commercial sources such as Avanti Polar Lipids (Alabaster, Ala.). The alcohol can be purchased from chemical suppliers such as Sigma Chemical Company (St. Louis, Mo.).

When combined together with the alcohol, the cardiolipin, lecithin, and cholesterol form a lipid matrix or micelle. As described in more detail below, antibodies associated with the presence of a human T. pallidum infection, referred to herein as anti-cardiolipin antibodies, bind to these lipid micelles and form antibody-antigen complexes. Therefore, the detection or measurement of these antibody-antigen complexes can be used to diagnose a T. pallidum infection. Although not wishing to be bound by the following hypothesis, it is believed that the anti-cardiolipin matrix antibodies bind to the synthetic antigen composition described herein with greater specificity and higher avidity than they bind to naturally occurring cardiolipin and lecithin. The synthetic antigen composition thereby provides a more efficient, more sensitive, and more specific means to detect antibodies associated with a syphilis infection.

It will be understood by those skilled in the art that one or more components of the antigen composition can be labelled with a detectable label to facilitate the direct measurement or detection of antibody-antigen complex formation. Various types of labels and methods of conjugating the labels to the antigen composition are well known to those skilled in the art.

Also, the antigen composition may be employed as a laboratory research tool to generate, isolate or purify anti-cardiolipin antibodies, and the antibodies can be used to study syphilis in general. Therefore, the antigen composition is useful for purposes such as in vivo and in vitro diagnostics and laboratory research.

Preparation of the VDRL Antigen

The VDRL antigen can be prepared, for example, by preparing an ethanolic solution of tetramyristoyl cardiolipin at a concentration by volume ranging from about 0.01-0.05%, or 0.02 to 0.04%, or more preferably 0.03%. An ethanolic solution of synthetic lecithin having a concentration by volume of approximately 0.11 to 0.16%, more preferably 0.14%, and an ethanolic solution of natural cholesterol of 0.9% are added to the cardiolipin solution. The components are added in the following sequence: cardiolipin, lecithin, cholesterol, and ethanol to volume. The antigen is solubilized and stored at room temperature over-night before testing.

Detection of Anti-Cardiolipin Antibodies

The method provided herein includes diagnostic and prognostic methods to detect and quantify antibodies capable of binding to the antigen composition described above. These methods permit detection of circulating antibodies to the cardiohpin-lecithin matrix in order to indicate the presence of T. pallidum infection and thereby diagnose infection or monitor the progress of an antibiotic in treating a T. pallidum infection.

There are many techniques known in the art for detecting or measuring antibody-antigen complexes, also referred to herein as immunocomplexes. Classical methods involve reacting a sample containing the antibody with a known excess amount of the antigen specific for the antibody, separating bound from free antigen, and determining the amount of bound antigen or free antigen. If free antigen is measured, the amount of bound antigen can be calculated by subtracting the amount of free antigen from the known starting amount. Often the antigen is directly or indirectly labeled with a reporter group or detectable label to aid in the determination of the amount of antibody-antigen complex as described herein. The reporter group or "label" is commonly a fluorescent or radioactive group or an enzyme. The label is then detected using methods well known to those skilled in the art such as spectrophotometry, scintillation counting, or flow cytometry.

Alternatively, the antigen can be conjugated to a solid phase bead or particle that is filtered, centrifuged, or otherwise removed from the mixture, such as by magnetically removing a metallic or magnetized particle. Attaching the antigen to solid phase beads, such as latex beads, provides a new more sensitive and rapid slide agglutination test.

In a preferred embodiment, the antigen is attached to the beads through the cardiolipin molecule. One method of attaching the antigen to the beads is to modify the cardiolipin molecule so that it can be covalently bonded to the beads. For example, an amine group can be attached to the terminal methyl groups of the fatty acid chains of the cardiolipin. Cardiolipin modified in this manner can be attached to carboxylated or aminealated latex beads.

A preferred immunoassay for the detection of anti-cardiolipin antibodies in a sample is performed as follows. A sample is collected or obtained using methods well known to those skilled in the art. The sample containing the anti-cardiolipin antibodies to be detected is obtained from a biological source. The sample is preferably obtained from a biological fluid, such as, but not limited to, whole blood, blood serum, blood plasma, saliva, cerebrospinal fluid, and the like. Optimal diagnostic results are obtained when the sample is serum or spinal fluid. The sample may be filtered or otherwise manipulated prior to immunoassay to optimize the immunoassay results.

The sample is then incubated with the antigen composition described herein to form an antibody-antigen immuno-complex. The antibody-antigen complex is then detected using methods well known to those skilled in the art. The term "detecting" or "detected" as used herein means using known techniques for detection of biologic molecules such as immunochemical or histological methods. Such methods include immunological techniques employing monoclonal or polyclonal antibodies to the lipids, such as enzyme linked immunosorbant assays (ELISA), sandwich assays, flow cytometric assays, radioimmunoassays, or other types of assays involving antibodies known to those skilled in the art.

In a preferred embodiment of the method, anti-cardiolipin antibodies in a sample are detected by employing the synthetic antigen composition described herein in a flocculation assay. Examples of known flocculation assays include the unheated serum reagin test (USR), the rapid plasma reagin 10 mm circle card test (RPR), the toluidine red unheated serum test (TRUST) and the VDRL slide assay. These assays are all flocculation tests. It will be understood by those skilled in the art that the anti-cardiolipin antibodies are also detectable using the antigen composition described herein in agglutination tests, which further employ carrier particles. In a more preferred embodiment of the method, the synthetic antigen composition is used in a VDRL slide assay as described briefly below and in more particularly in Venereal Disease Research Laboratory (VDRL) Slide Test, Kennedy, E. J. Jr. and Creighton, E. T., 157-78 (1998) in A Manual of Tests for Syphilis, $9^{th}$ ed., Larsen, S. A., Pope, V., Johnson, R. E. and Kennedy, E. J. Jr. (Eds.), American Public Health Association, Washington, D.C., which is incorporated by reference herein.

The VDRL slide assay is performed as follows. VDRL-buffered saline containing formaldehyde, $Na_2HPO_4$, $KH_2PO_4$ , NaCl and distilled water, is placed in a vessel. The antigen composition is added slowly to the saline at a constant rate while rotating the vessel and the mixture is then agitated to thoroughly combine the contents and form a suspension. The sample, such as serum, is placed into a ring of a paraffin or ceramic-ringed slide and one drop of the antigen composition suspension is added. The slide is rotated to mix the sample and antigen composition and is then read microscopically. The presence of clumps, clumping or roughness indicates antibody-antigen formation. Serial dilutions of the antigen suspension can be used for a qualitative measurement of antibody in the sample. Quantitative determinations can be made by performing the assay with standard concentrations of antibody and comparing the results of the sample with the results generated by the standards.

It is to be understood that the assay methods are contemplated to include the use of synthetic antigen compositions as described above and synthetic derivatives of the antigen compositions described herein provided that the derivatives retain antigenic activity or display an equivalent antigenic activity and have specificity for anti-cardiolipin antibodies.

Kit for Detecting the Presence of T. pallidum

A kit for diagnosing or otherwise evaluating a syphilis infection by detecting the presence or quantity of anti-cardiolipin antibodies is also provided. The kit can be in any configuration well known to those of ordinary skill in the art and is useful for performing one or more of the methods described herein for the detection of anti-cardiolipin-lecithin matrix antibodies in biological samples or for the detection or monitoring of T. pallidum infection in a patient or carrier. The kits are convenient in that they supply many if not all of the essential reagents for conducting an assay for the detection of syphilis antibodies in a biological sample. The reagents may be pre-measured and contained in a stable form in vessels or on a solid phase in or on which the assay may be performed, thereby minimizing the number of manipulations carried out by the individual conducting the assay. In addition, the assay may be performed simultaneously with a standard that is included with the kit, such as a predetermined amount of antibody, so that the results of the test can be validated or measured.

The kit preferably contains the antigen composition described herein, which can be used for the detection of cardiolipin antibodies associated with T. pallidum infection. The kit also preferably contains cholesterol and can additionally contain the appropriate reagents that aid in detecting antibody-antigen complexes. The kit may additionally contain equipment for safely obtaining the sample, a vessel for containing the reagents, a buffer for diluting the sample or reagents, and circle cards such as the 10 mm slides or 18 mm circle cards used in VDRL, RPR and TRUST assays.

The assay kit includes but is not limited to reagents to be employed in the following techniques; flocculation tests such as USR, RPR and TRUST; agglutination assays; and sandwich or ELISA assays. Materials used in conjunction with these techniques include, but are not limited to, micro-titer plates, antibody-coated strips or dipsticks for rapid monitoring of biological fluids. For each kit, the range, sensitivity, precision, reliability, specificity and reproducibility of the assay are established. Standardization may be achieved using reference control sera and titering the sera to endpoint or a panel of sera may be utilized.

In a more preferred embodiment, the assay kit uses VDRL slide techniques and provides instructions and the antigen composition described above. The kit is useful for the measurement of T. pallidum infection, and more specifically, for the measurement of antibodies directed toward cardiolipin in biological fluids of humans exhibiting symptoms of syphilis or those at risk for syphilis infection.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of a Synthetic Cardiolipin and Lecithin Composition

Tetramyristoyl cardiolipin, purified by silica gel chromatography to approximately 99% purity, was obtained in powder form from Avanti Polar Lipids (Alabaster, Ala.). The final concentration of sodium salt was tested for purity by thin layer chromatography and high-pressure liquid chromatography. The sample was stored at −20° C. The tetramyristoyl cardiolipin was originally synthesized from semi-synthetic lipid precursors that originated from a plant source.

Lecithin (1-palmitoyl-2-oleoyl-sn-glycero-phosphocholine) powder, purified by silica gel chromatography to a purity of approximately 99%, was also obtained from Avanti Polar Lipids. The lecithin was originally isolated from soybeans.

A 1.2% solution of cholesterol (Avanti Polar Lipids) in absolute ethanol was prepared and filtered with alcohol-rinsed filter paper #560. The cholesterol was originally derived from wool grease and purified by re-crystallization, and the crystals were stored at −20° C.

An antigen composition was prepared by combining the synthetic cardiolipin with the synthetic lecithin, the cholesterol solution and the ethanol, in that order. The final concentration of synthetic cardiolipin was 0.02-0.03% by volume. The final concentration of synthetic lecithin was 0.11-0.16% by volume. The final concentration of cholesterol was 0.9% by volume and the remainder of the antigen composition was the ethanol.

EXAMPLE 2

Comparative Analysis of Synthetic VDRL Slide Assay versus Conventional VDRL Slide Assay The sensitivity of the VDRL slide assay using the synthetic cardiolipin and lecithin composition described in Example 1 was compared with the sensitivity of the conventional VDRL slide assay as described in A Manual of Tests for Syphilis, 9$^{th}$ ed., 159-77, Larsen, S. A., Pope, V., Johnson, R. E. and Kennedy, E. J. Jr. (Eds.), American Public Health Association, Washington, D.C. Briefly, 0.4 ml VDRL-buffered saline (formaldehyde, $Na_2HPO_4$, $KH_2PO_4$, NaCl and distilled water) was added to the bottom of a round 30 ml glass-stoppered bottle with a flat inner-bottom surface or a 25 ml glass-stoppered Erlenmeyer flask. Subsequently, 0.5 ml of the antigen composition suspension was added directly to the saline at a rate of 6 seconds/0.5 ml of antigen suspension while rotating the bottle continuously. Rotation continued for ten seconds until 4.1 ml of buffered saline was added. The bottle was tightly capped and shaken from bottom to top approximately thirty times in ten seconds. The antigen suspension was used within eight hours.

The qualitative tests were performed by placing 50 μl of serum into one ring of a paraffin or ceramic-ringed slide using a safety pipetting device. The antigen suspension was gently re-suspended and one free-falling drop (17 μl) was added. The slide was placed on a mechanical rotator for four minutes at 180±2 rpm. The slide was immediately removed and read microscopically using 10× oculars and a 10× objective. Results were reported as follows: reactive—medium or large clumps, weakly or minimally reactive—small clumps, non-reactive—no clumping or a very slight roughness. Quantitative tests were similarly performed with serial two-fold dilutions of the serum.

The results, set forth below in Table 1, indicated that the test using the synthetic antigen composition was more sensitive than the test using the standard VDRL antigen, which was made using natural cardiolipin and lecithin.

TABLE 1

Comparison of Sensitivities of Natural VDRL versus Synthetic VDRL Assays

| Test | Sensitivity Primary | Secondary | Latent |
|---|---|---|---|
| Natural VDRL | 80% | 100% | 85% |
| Synthetic VDRL | 84% | 100% | 88% |

The sensitivities of the VDRL slide assay using the synthetic cardiolipin and lecithin antigen composition described in Example 1 and the conventional VDRL slide assay were also compared against the conventional RPR slide assay. As shown in Tables 2 and 3 below, the assay using the synthetic VDRL antigen composition was more reactive with samples that tested positive using the RPR test than the assay using the non-synthetic VDRL antigen.

TABLE 2

RPR versus Synthetic VDRL

| RPR | Synthetic VDRL Reactive | Nonreactive |
|---|---|---|
| Reactive* | 41 | 13 |
| Nonreactive | 1 | 5 |

*All RPR reactives were minimally reactive

TABLE 3

| RPR versus Natural VDRL | | |
|---|---|---|
| | Natural VDRL | |
| RPR | Reactive | Nonreactive |
| Reactive* | 13 | 41 |
| Nonreactive | 0 | 6 |

*All RPR reactives were minimally reactive

EXAMPLE 3

Comparative Analysis of Synthetic VDRL antigen and Natural VDRL antigen (Qualitative Test)

Samples from 100 frozen banked sera, reactive by the nontreponemal (RPR) test, were used to compare the CDC synthetic VDRL antigen and a reference VDRL antigen (Natural VDRL antigen). The serum samples were heat inactivated for 30 minutes at 56° C. Fifty microliters of each serum sample was placed into a corresponding paraffin or ceramic-ringed slide. A drop (17 μL) of each of the antigens was placed in the corresponding rings of the slide. The slides were placed in a mechanical rotator and rotated for 4 minutes at 180 rpm and then read microscopically. The degree of flocculation of the two antigens was observed and recorded.

As reported in Table 4 (undocumented) all of the sera (100%), reactive by RPR, were reactive with the CDC synthetic VDRL antigen while only 88% were reactive with the natural VDRL antigen.

Additionally, the synthetic VDRL antigen and the natural VDRL antigen were compared in the same test using 100 samples from documented syphilis cases. The results of this test are also shown in Table 4 (documented). All of the results from these tests were confirmed by the SERODIA Treponema pallidum particle agglutination test (TP-PA) (Fujirebio America, Inc., Fairfield, N.J.).

TABLE 4

| | | | Number of serum samples reactive with | | |
|---|---|---|---|---|---|
| Syphilis Category | | Number of Serum Samples | Synthetic VDRL antigen | Natural VDRL antigen | TP-PA |
| Undocumented | | 100 | 100 | 88 | 99 |
| Documented | | | | | |
| Untreated | Primary | 9 | 9 | 9 | 8 |
| | Secondary | 20 | 20 | 20 | 20 |
| | Latent | 6 | 5 | 5 | 6 |
| Treated | Primary | 15 | 12 | 11 | 13 |
| | Secondary | 30 | 30 | 30 | 30 |
| | Latent | 20 | 18 | 17 | 19 |
| Total | | 200 | 194 | 180 | 195 |

EXAMPLE 4

Comparative Analysis of Synthetic VDRL Antigen and Natural VDRL Antigen (Quantitative Test)

Samples from 100 frozen banked sera, reactive by the nontreponemal (RPR) test, were used to compare the CDC synthetic VDRL antigen and a reference VDRL antigen (Natural VDRL antigen). The serum samples were diluted two-fold in a test tube with 0.9% saline. Fifty microliters of each of the tube dilutions was transferred to the corresponding rings of a ceramic or paraffin-ringed slide. A drop (17 μL) of each of the antigens was placed in the corresponding rings of the slide. The slides were placed in a mechanical rotator and rotated for 4 minutes at 180 rpm. The endpoint titer of each of the serum dilutions was read microscopically. One doubling dilution difference was defined as an endpoint either (R) from one antigen or (N) for the other antigen.

As seen in Table 5 (undocumented), this test showed that 85% of the frozen banked sera reactive in the RPR test had end-point titers of one half or one dilution greater with CDC synthetic VDRL antigen than with natural VDRL antigen. In 15% of the cases, the end-point titer obtained with the CDC synthetic VDRL antigen was equal to that obtained with the natural VDRL antigen. In none of the samples tested was the end-point titer greater with the natural antigen than with the CDC synthetic antigen.

This test was repeated using 100 samples from documented syphilis cases. As seen in Table 5 (documented), 84% of the sera from documented syphilis cases had end-point titers of one half or one dilution greater with CDC synthetic VDRL antigen than with natural VDRL antigen. In 7% of the cases, the end-point titer obtained with the CDC synthetic VDRL antigen was equal to that obtained with the natural VDRL antigen, while in 3% of the cases the end-point titer of the natural VDRL antigen was one half or one dilution greater than that of the CDC synthetic VDRL antigen. The results of these tests were confirmed by TP-PA test.

TABLE 5

| Syphilis Category | | Number of Specimens | CDC Synthetic VDRL antigen higher | Natural VDRL antigen higher | CDC synthetic and Natural VDRL antigens equal endpoints |
|---|---|---|---|---|---|
| Undocumented | | 100 | 85 | 0 | 0 |
| Documented | | | | | |
| Untreated | Primary | 9 | 3 | 2 | 4 |
| | Secondary | 20 | 20 | 0 | 0 |
| | Latent | 6 | 4 | 0 | 1 |
| Treated | Primary | 15 | 10 | 0 | 2 |
| | Secondary | 30 | 30 | 0 | 0 |
| | Latent | 20 | 17 | 1 | 0 |
| Total | | 200 | 169 | 3 | 7 |

EXAMPLE 5

Comparative Analysis of Synthetic VDRL Antigen and Natural VDRL Antigen (Qualitative Test) in Patients Having Diseases Other than Syphilis Samples from 100 patients having diseases other than syphilis were qualitatively tested using the procedure of Example 3. These tests were confirmed by the TP-PA test and the FTA-ABS test. The results of these tests are reported in Table 3 which shows that all of the samples were nonreactive with both the CDC synthetic VDRL antigen and the natural VDRL antigen. Four of the samples were reactive in the TP-PA test, but nonreactive in the FTA-ABS test.

TABLE 6

| Category of Sample | Number of Specimens | Number of serum samples reactive and nonreactive: CDC Synthetic VDRL antigen R | CDC Synthetic VDRL antigen N | Becton Dickinson VDRL antigen R | Becton Dickinson VDRL antigen N | TP-PA R | TP-PA N | FTA-ABS R | FTA-ABS N |
|---|---|---|---|---|---|---|---|---|---|
| Rheumatic Fever | 27 | 0 | 27 | 0 | 27 | 4 | 23 | 0 | 27 |
| Coronary Arterial Disease | 9 | 0 | 9 | 0 | 9 | 0 | 9 | ND | |
| Hypertension | 6 | 0 | 6 | 0 | 6 | 0 | 6 | ND | |
| Diabetes | 4 | 0 | 4 | 0 | 4 | 0 | 4 | ND | |
| Parkinson's | 2 | 0 | 2 | 0 | 2 | 0 | 2 | ND | |
| Obesity | 2 | 0 | 2 | 0 | 2 | 0 | 2 | ND | |
| Angina | 2 | 0 | 2 | 0 | 2 | 0 | 2 | ND | |
| Miscellaneous | 48 | 0 | 48 | 0 | 48 | 0 | 48 | ND | |
| Category Total Number | 100 | 0 | 100 | 0 | 100 | 4 | 96 | | |

R = reactive; N = nonreactive

EXAMPLE 6

Comparative Analysis of Synthetic VDRL Antigen and Natural VDRL Antigen (Qualitative Test) in Biological False Positive Samples Samples were obtained from 50 individuals that were originally classified as biological false positives (BFP). These individuals tested nontreponemal test reactive and treponemal test nonreactive. These samples were tested using the procedure of Example 3. The results of this test is shown in Table 7. Four of the serum samples that were originally misclassified as BFP were found reactive with the CDC synthetic VDRL antigen, the TP-PA, and the FTA-ABS tests. Three of these four samples were also reactive with the natural VDRL antigen.

TABLE 7

| Reactivity of Sample | TP-PA | CDC synthetic VDRL antigen | Natural VDRL antigen |
|---|---|---|---|
| Reactive | 4 | 28 | 27 |
| Nonreactive | 46 | 22 | 23 |

R = reactive; N = nonreactive

EXAMPLE 7

Comparative Analysis of Synthetic VDRL Antigen and Natural VDRL Antigen (Qualitative Test) in Unknown Samples 495 samples with no patient identifiers were tested with CDC synthetic VDRL antigen and natural VDRL antigen using the procedure in Example 3 above. Reactive specimens were confirmed with the TP-PA test, the ELISA test for syphilis IgG antibody, or the FTA-ABS test. Thirty-eight of the samples were reactive in one of the treponemal tests and 457 were nonreactive. As can be seen in Table 8, all of the samples that were treponemal reactive were reactive with the CDC synthetic VDRL antigen and 36 were reactive with the natural VDRL antigen. Of the 457 serum samples that were treponemal nonreactive, 452 were nonreactive with the CDC synthetic VDRL antigen and 450 were nonreactive with the natural VDRL antigen.

TABLE 8

| | Number of Tests | CDC synthetic VDRL antigen R | CDC synthetic VDRL antigen N | Natural VDRL antigen R | Natural VDRL antigen N |
|---|---|---|---|---|---|
| Reactive | 38 | 38 | 0 | 36 | 2 |
| Nonreactive | 457 | 5 | 452 | 7 | 450 |

R = reactive; N = nonreactive

We claim:

1. An antigen composition comprising *between 0.01 and 0.05% by volume* tetramyristoyl cardiolipin and *between 0.11 and 0.16% by volume* 1-palmitoyl-2-oleoyl-sn-glycero-3-phosphocholine.

2. The antigen composition of claim 1, further comprising cholesterol.

3. The composition of claim 2, wherein the *volume* concentration of cholesterol is 0.9%.

4. The composition of claim 2, further comprising an alcohol.

5. The composition of claim 1, wherein the concentration of cardiolipin is between 0.02 and 0.04%.

6. The composition of claim 5, wherein the *volume* concentration of cardiolipin is 0.03%.

[7. The composition of claim 1, wherein the concentration of 1-palmitoyl-2-oleoyl-sn-glycero-3-phosphocholine is between 0.11 and 0.16%.]

8. The composition of claim [7] *1*, wherein the *volume* concentration of 1-palmitoyl-2-oleoyl-sn-glycero-3-phosphocholine is 0.14%.

9. The composition of claim 4, wherein the alcohol is ethanol.

10. A method for detecting anti-lipoidal antibodies in a human comprising combining a biological sample from the human with a composition comprising tetramyristoyl cardiolipin and 1-palmitoyl-2-oleoyl-sn-glycero-3-phosphocholine and detecting an immunocomplex formed between an anti-lipoidal antibody in the biological sample and the composition.

11. The method of claim 10, wherein the composition further comprises cholesterol and an alcohol.

12. The method of claim 11, wherein the *volume* concentration of cholesterol in the composition is 0.9%.

13. The method of claim 10, wherein the alcohol is ethanol.

14. The method of claim 10, wherein the *volume* concentration of tetramyristoyl cardiolipin in the composition is between 0.01 and 0.05%.

15. The method of claim 10, wherein the *volume* concentration of 1-palmitoyl-2-oleoyl-sn-glycero-3-phosphocholine in the composition is between 0.11 and 0.16%.

16. The method of claim 10, wherein the detection of an immunocomplex is used to diagnose syphilis in the human.

17. The method of claim 10, wherein the immunocomplex is detected using a flocculation or agglutination test.

[18. The antigen composition of claim 1 comprising between 0.02 and 0.04% tetramyristoyl cardiolipin, and between 0.11 and 0.16% 1-palmitoyl-2-oleoyl-sn-glycero-3-phosphocholine.]

19. An antigen composition comprising between 0.02 and 0.04% *by volume* tetramyristoyl cardiolipin, between 0.11 and 0.16% *by volume* 1-palmitoyl-2-oleoyl-sn-glycero-3-phosphocholine, 0.9% *by volume* cholesterol, and ethanol to volume.

20. An antigen composition comprising 0.03% *by volume* tetramyristoyl cardiolipin, between 0.11 and 0.16% *by volume* 1-palmitoyl-2-oleoyl-sn-glycero-3-phosphocholine, and 0.9% *by volume* natural cholesterol in absolute ethanol to volume.

21. A method for detecting anti-lipoidal antibodies in a human comprising:

(a) obtaining a biological sample from a human;

(b) combining the biological sample with a composition comprising between 0.02 and 0.04% *by volume* tetramyristoyl cardiolipin, between 0.11 and 0.16% *by volume* 1-palmitoyl-2-oleoyl-sn-glycero-3-phosphocholine, 0.9% *by volume* cholesterol, and ethanol to volume; and (c) detecting an immunocomplex formed between an antibody in the biological sample and the composition.

22. The method of claim 21, wherein the detection of the immunocomplex is used to diagnose syphilis in the human.

23. The method of claim 10, wherein the *volume* concentration of tetramyristoyl cardiolipin in the composition is between 0.02 and 0.04%.

*24. An antigen composition consisting of tetramyristoyl cardiolipin, 1-palmitoyl-2-oleoyl-sn-glycero-3-phosphocholine, cholesterol, and an alcohol.*

*25. The composition of claim 24, wherein the volume concentration of tetramyristoyl cardiolipin is between 0.01 and 0.05%, the volume concentration of 1-palmitoyl-2-oleoyl-sn-glycero-3-phosphocholine is between 0.11 and 0.16%, and the volume concentration of cholesterol is 0.9%.*

*26. The composition of claim 25, wherein the volume concentration of tetramyristoyl cardiolipin is between 0.02 and 0.04%.*

* * * * *

UNITED STATES PATENT AND TRADEMARK OFFICE

CERTIFICATE OF CORRECTION

PATENT NO. : RE43,914 E
APPLICATION NO. : 13/333849
DATED : January 8, 2013
INVENTOR(S) : Arnold R. Castro It is certified that error appears in the above-identified patent and that said Letters Patent is hereby corrected as shown below:

On page 1 of the Title Page:

Left hand column 1, line 2, under FOREIGN PATENT DOCUMENTS, "JP 74046051 B * 7/1974" should be deleted.

Left hand column 1, line 6, under FOREIGN PATENT DOCUMENTS, "SE 629927 * 10/1978" should be deleted.

Right hand column 2, lines 39-48, under OTHER PUBLICATIONS, the four citations listed below are duplicate citations and should be deleted:

"Avanti Polar Lipids Inc. Products # 850457 and 710332.*"

"Gokhale et al. Brithish Journal of Cancer, vol. 74, pp. 43-48 1996.*"

"Gokhale, P.C. et al., 'An Improved Method of Encapsulation of Doxorubicin in Liposomes: Pharmacological, Toxicological and Therapeutic Evaluation,' *British Journal of Cancer*, vol. 74, No. 1, pp. 43-48 (1996)."

"Inoue, K. et al., 'Immunochemical Studies of Phospholipids–IV: The Reactivities of Antisera Against Natural Cardiolipin and Synthetic Cardiolipin Analogues-Containing Antigens,' *Chemistry and Physics of Lipids*, vol. 3, No. 1, pp. 70-77 (1969).".

On page 2 of the Title Page:

Left hand column 1, lines 1-7, under OTHER PUBLICATIONS, the two citations listed below are duplicate citations and should be deleted:

"Browne, A.S. et al., 'An Evaluation of the Cardiolipin-Synthetic Lecithin Kline Test,' *Technical Bulletin of the Registry of Medical Technologists*, vol. 33, No. 10, pp. 171-176 (Oct. 1963)."

Signed and Sealed this
Tenth Day of December, 2013

Margaret A. Focarino

Margaret A. Focarino
*Commissioner for Patents of the United States Patent and Trademark Office*

"Castro, A.R. et al., 'Use of Synthetic Cardiolipin and Lecithin in the Antigen Used by the Venereal Disease Research Laboratory Test for Serodiagnosis of Syphilis,' *Clinical and Diagnostic Laboratory Immunology*, vol. 7, No. 4, pp. 658-661 (Jul. 2000).".

Right hand column 2, lines 1-5, under OTHER PUBLICATIONS, the two citations listed below are duplicate citations and should be deleted:

"Wicher, K. et al., 'Autoimmunity in Syphilis,' *Immunol Ser*, vol. 52, pp. 101-124, Abstract (1990)."

"Paris-Hamelin, A. et al., '[Immunoblotting for the Serodiagnosis of Syphilis. A Candidate to Replace the Nelson-Mayer Test],' Ann Pharm Fr., vol. 57, No. 1, pp. 68-75, Abstract (1999).".